United States Patent [19]

Nudelman et al.

[11] Patent Number: 5,227,160
[45] Date of Patent: Jul. 13, 1993

[54] MONOCLONAL ANTIBODY NUH2 CAPABLE OF INACTIVATING MOTILITY OF HUMAN SPERM, ANTIGEN DEFINED BY SAID MONOCLONAL ANTIBODY AND METHODS OF USING SAID MONOCLONAL ANTIBODY AND ANTIGEN

[75] Inventors: Edward Nudelman; Tokio Kaizu; Ulla Mandel-Clausen; Steven B. Levery; Sen-itiroh Hakomori, all of Seattle, Wash.; Yoshiyuki Tsuji; Shinzo Isojima, both of Hyogo, Japan

[73] Assignees: The Biomembrane Institute, Seattle, Wash.; Hyogo Medical College, Hyogo, Japan

[21] Appl. No.: 219,401

[22] Filed: Jul. 15, 1988

[51] Int. Cl.$^5$ ............... A61K 39/00; A61K 35/14; H01L 49/00; H01L 21/20
[52] U.S. Cl. ............... 424/85.9; 424/88; 437/7; 437/89; 530/387.5; 530/388.2; 514/843
[58] Field of Search ............... 424/85.9, 88; 514/12, 514/843; 437/7; 530/387

[56] References Cited

U.S. PATENT DOCUMENTS

| | | | |
|---|---|---|---|
| 4,795,634 | 1/1989 | Grimes et al. | 424/85.9 |
| 5,051,251 | 9/1991 | Morita et al. | 424/70 |
| 5,051,425 | 9/1991 | Nakai | 514/256 |
| 5,051,445 | 9/1991 | Louis et al. | 514/459 |

OTHER PUBLICATIONS

Pharmaceutical Technology, Parrott, Burgess Publ. Co., MN, 1970.
Selected Methods in Cellular Immunology, Mishell & Shiigi, W. H. Freeman, S. F., 1980.
Essential Immunology, Roitt, Blackwell, Oxford, 1971.

*Primary Examiner*—Frederick E. Waddell
*Assistant Examiner*—T. J. Criares
*Attorney, Agent, or Firm*—Sughrue, Mion, Zinn, Macpeak & Seas

[57] ABSTRACT

Monoclonal antibody NUH2 produced by a hybridoma having ATCC deposit no. HB 9762. An isolated antigen capable of specifically binding to anti-human sperm antibodies including NUH2 and comprising at least an epitope having a sialyl I structure, and any analogues derived from said antigen. Methods of using the monoclonal antibody and antigen for contraception and treating infertility in human females.

7 Claims, 4 Drawing Sheets

FIG. 4

MONOCLONAL ANTIBODY NUH2 CAPABLE OF INACTIVATING MOTILITY OF HUMAN SPERM, ANTIGEN DEFINED BY SAID MONOCLONAL ANTIBODY AND METHODS OF USING SAID MONOCLONAL ANTIBODY AND ANTIGEN

FIELD OF THE INVENTION

The present invention relates to a novel monoclonal antibody capable of inactivating motility of human sperm and to the antigen defined by the monoclonal antibody. The monoclonal antibody and antigen are useful for developing new methods of birth control as well as new methods of treating sterility in women caused by the presence of anti-sperm antibodies in their serum.

BACKGROUND OF THE INVENTION

Although female sterility has been induced in experimental animals by active immunization with sperm (Isojima, S., et al (1959) *Science* 129:44; Katsh, S. (1959) *Am. J. Obstet. Gynecol.* 78:276), and antibodies that react with human sperm have been found to be present in sera of infertile women (Franklin, R. R., and C. D. Dukes (1964) *Am. J. Obstet. Gynecol.* 89:6), no strong correlation has been found between the presence of such antibodies and naturally-occurring human female infertility (Tyler, A., et al (1967) *Fertil. Steril.* 18:153; Israelstam, D. M. (1969) *Fertil. Steril.* 20:275). However, Isojima et al (Isojima, S., et al (1968) *Am. J. Obstet. Gynecol.* 101:677) reported the finding that sera of infertile women inactivates human sperm motility in the presence of guinea pig complement. Approximately 17% of infertile women due to unknown causes had antibodies in their sera that inactivated human sperm motility in the presence of complement. No such antibody was detectable in sera of parous women. These findings led to a generally accepted hypothesis that the presence of such antibodies in sera of infertile women can be regarded as the cause of female infertility (Isojima, S., et al (1972) *Am. J. Obstet. Gynecol.* 112:199). Thus, the specificities and immunobioligical properties of antibodies present in sera of infertile women showing complement-dependent inactivation of sperm motility are of crucial importance for understanding the biological mechanism of female infertility. However, the activity of such antibodies in sera of infertile women is generally lower than a sperm immobilization titer of 1:200 ("200 SI$_{50}$") (Isojima, S., and K. Koyama (1976) *Excerpta Med. Intern. Congr. Ser.* 370:11), and certain serum components of normal subjects showed non-specific binding with human sperm. Therefore, immobiological studies on infertility have been difficult to perform in further detail.

SUMMARY OF THE INVENTION

Accordingly, one object of the present invention is to provide a monoclonal antibody that induces sperm immotility.

A second object of the present invention is to provide an isolated antigen to which the above-described monoclonal antibody is specific and to elucidate the chemical properties of this antigen.

A third object of the present invention is to provide novel vaccines, preparations and methods for birth control in humans.

A fourth object of the present invention is to provide a method for detecting the presence of anti-sperm antibodies in the sera of infertile women.

A fifth object of the present invention is to provide a method for treatment of infertility caused by the presence of anti-sperm antibodies in the serum of infertile women.

These and other objects have been accomplished by providing a monoclonal antibody NUH2 produced by a hybridoma having ATCC deposit no. HB 9762.

The present invention also provides a method of inactivating human sperm motility comprising contacting said sperm with monoclonal antibody NUH2 in the presence of complement.

This method can be adapted for use in contraception and thus the present invention provides a method of vaginal contraception comprising contacting human sperm in the presence of complement with a contraceptive composition comprising a human sperm inactivating amount of monoclonal antibody NUH2, and a pharmaceutically acceptable carrier, diluent or excipient.

The present invention also provides the above-described contraceptive composition.

In another embodiment the present invention provides an isolated antigen capable of specifically binding to anti-human sperm antibodies including NUH2 and comprising at least an epitope having a sialyl I structure, and any analogues derived from said antigen. (Unless otherwise specified the term "sialyl I" based herein refers to "disialyl I".)

This antigen can be used to provide a method of contraception comprising inducing an anti-sperm immune response in human females by administering a vaccine comprising:

(a) a pharmaceutically effective amount of an antigen capable of inducing anti-human sperm antibody NUH2 and which comprises a sialyl I structure, and (b) a pharmaceutically acceptable carrier, diluent or excipient.

The above described contraceptive vaccine is also provided.

Further the present invention provides a method of detecting anti-sperm antibodies present in the sera of infertile human females comprising:

(a) taking a blood sample from the infertile female, (b) contacting the blood sample with an antigen capable of specifically binding to anti-human sperm antibody NUH2 and comprising the sialyl I structure, and (c) detecting the presence of any antigen-anti-sperm antibody complexes.

Finally, a method of treating infertile human females whose infertility is caused by the presence of anti-sperm antibodies in the female's sera is provided comprising:

(a) contacting the sera ex vivo with an antigen having epitopes to anti-human sperm antibodies and comprising sialyl I, i and sialyl i structures to thereby form an anti-sperm antibody-antigen complex between said antibodies and said antigens such that said antibodies are removed from said sera, and (b) recycling said contacted sera to said female.

BRIEF DESCRIPTION OF THE DRAWINGS

FIG. 1 is a series of graphs showing the reactivities of human sperm cells with various monoclonal antibodies directed to neolactoseries structures, before and after sialidase treatment as described in Example 1. Reactivities are identified in each panel. In FIG. 1B 6C defines structure I, i.e., lactoisooctaosylceramide; In FIG. 1D 1B9 defines 2→6 sialylparagloboside; In FIG. 1E 1B2 specifies terminal N-acetyllactosamine as in nLc$_4$, nLc$_6$, and nLc$_8$.

FIG. 2 is a graph showing the reactivity of NUH2 antibody with various glycolipid structures. The reactivity was determined by solid-phase antibody-binding assay on glycolipid-coated plastic wells. The ordinate represents $^{125}$I-labeled antibody binding. The abscissa represents serial dilutions of antigen, with 1=100 ng antigen per well, 2=50 ng antigen per well, etc. Baseline, showing no reactivity, includes GM$_2$ ganglioside, sialyl 2=3 paragloboside, sialyl 2→6 paragloboside, sialyl 2→3 norhexaosylceramide, sialyl 2→6 norhexaosylceramide, sialidase-treated disialosyl I, sialidase-treated fraction 90–102 ganglioside and sialidase-treated fraction 72–77 ganglioside. The open circles represent disialyl I. The open squares represent fraction 90–102 ganglioside (isolated from placenta). The open triangles represent fraction 72–77 ganglioside (isolated from placenta).

DETAILED DESCRIPTION OF THE INVENTION

According to the present invention there is provided a monoclonal antibody designated NUH2 that specifically reacts with human sperm, and in particular reacts with an antigen that carries the sialyl I structure.

The hybridoma that produces the monoclonal antibody NUH2 has been deposited with the American Type Culture Collection in Rockville, Maryland and has ATCC deposit no. HB 9762.

The monoclonal antibody NUH2 was established in the process of trying to develop monoclonal antibodies to human tumor antigens. The inventors immunized mice with the disialosyl ganglioside fraction from human adenocarcinoma, wherein the gangliosides were coated on acid-treated *Salmonella minnesotae* according to known methods and then spleen cells of the immunized mice were fused with mouse myeloma SP1 cells also according to known methods. The hybridoma that produces monoclonal antibody NUH2 was established by selecting for reaction with specific gangliosides. The inventors then unexpectedly found that the monoclonal antibody NUH2 reacts with human sperm such that the motility of the human sperm is inactivated.

The isotype of monoclonal antibody NUH2 is IgM.

A detailed analysis of monoclonal antibody NUH2 was carried out by testing the reactivity to various glycolipids with known structures by known methods and as a result monoclonal antibody NUH2 can be further characterized as specifically reacting with disialyl I structures. Further monoclonal antibody NUH2 does not react with sialyl i structures, i structures, monosialyl I structures or I structures.

The disialyl I, sialyl i, i, monosialyl I and I structures are shown below. In the structures and throughout this application, glycolipids are abbreviated according to the recommendations of the IUPAC Committee on Biochemical Nomenclature (*Biochem. J.* 171:21-35, 1978), but the suffix "OseCer" is omitted

Disialyl I

Sialyl i wherein n = 1, 2 or more;

i wherein n = 1, 2 or more;

Monosialyl I or

I

In all of the above structures, R represents any structure that can bind to sialyl I, sialyl i, i, monosialyl I, and I. In naturally occurring structures, R represents (a), (b), (c) or (d) shown below:

When the molecule is a glycospingolipid, R is structure (a) or (b). When the molecule is a glycoprotein, R is structure (c) or (d) or their variants. Structures for glycoprotein cores and their variants are disclosed in Kornfeld, R. and Kornfeld, S. "Biochemistry of Glycoproteins and Proteoglycans", pp 1–27, edited by W. J. Lenner, Plenum Press, New York and London, 1980.

Structure I defined above is a type of histo-blood group antigen present in red blood cells and many other tissues in adults, and consists of a branched type 2 chain. The i structure is essentially absent in adult tissue but is present in fetal red blood cells and is converted to the I structure after birth. The i structure is an unbranched repeated type 2 chain N-acetyllactosamine.

The antigen from human sperm and placenta to which monoclonal antibody NUH2 is specific has been isolated and characterized and this antigen constitutes a further aspect of the present invention.

Chemical analysis of the antigen defined by monoclonal antibody NUH2 has been carried out by nuclear magnetic resonance spectroscopy and mass spectroscopy of the permethylated compound. The antigen has been identified as a group of compounds carrying the sialyl I structure as one epitope. The antigen also carries the sialyl i structure and the i structure.

The antigen can be isolated from human sperm by conventional methods usually applied for isolation of glycoproteins and glycolipids from tissues such as those described in Example 3 below.

The antigen can also be isolated from human placenta by the method used to isolate the antigen from sperm except that the starting material is homogenated human placenta tissue prepared by methods readily determined by the skilled artisan.

Further, as demonstrated in Example 3 below, the antigen comprises one or more groups of molecules having molecular weights, as determined by Sephadex gel filtration of 240 KDa, 180 KDa and 140KDa.

These three groups of molecules can be further purified and consolidated into one peak by Con A-Sepharose chromatography also by conventional methods such as those described in Example 3.

Further, with the application of synthetic organic chemistry (David, S. and Thieffrv, A. *J. Chem. Soc.* *Perkins Transaction I* (1977) pp 1568–1573; Alais, J. and Veyrieres,, A. *J. Chem. Soc. Perkins Transaction I* (1981) pp 377–381), the antigen can be synthesized once the entire sequence is determined, and such synthetic antigens are included within the scope of this invention along with any analogues derived from the antigens, including extension of chains and linking of the antigen or epitopic structures to solid phase or other supporting material.

While not wanting to be bound by the following explanation, the present inventors suspect that distribution of i or $\alpha2\rightarrow3$ sialyl-i organized in high density, which is defined by enhanced reactivity with anti-i antibodies after sialidase treatment, must be highly limited in normal tissue. Similarly, distribution of $\alpha2\rightarrow3$ sialyl-I must also be limited, even though the I structure is commonly expressed in a variety of tissues, particularly those of mesodermal origin. Native sperm cells may be unique in having a high density of $\alpha2\rightarrow3$ sialyl-i as well as $\alpha2\rightarrow3$ sialyl-I structure. Such a structural profile constitutes a susceptible receptor to complement-dependent inactivation of sperm motility. The molecule defined by monoclonal antibody NUH2 can be found in both glycosphingolipids and glycoproteins.

As mentioned above the monoclonal antibody NUH2 shows strong immobilizing activity of human sperm in the presence of complement. This is demonstrated in Example 1 below and shown in Table 1.

Thus a further aspect of the present invention comprises a method of inactivating human sperm motility comprising contacting said sperm with monoclonal antibody NUH2 in the presence of complement.

Depending upon the use of the method, the complement is either provided in vitro, for example as a component of guinea pig serum, or in vivo by the human body.

Complement is a term of art describing a group of proteins active in various immunological phenomena particularly when antibodies are bound to membrane antigens which cause damage of the cell membrane in the presence of a series of complements. The definition is well understood by the skilled artisan.

The amount of monoclonal antibody NUH2 and complement, whether provided in vitro or in vivo, sufficient to inactivate sperm motility can readily be determined by the skilled artisan, particularly by reference to Example 1 herein.

The method for immobilizing sperm motility, has many practical applications including a method of contraception for humans.

Accordingly, the present invention provides a method of contraception for humans comprising contacting human sperm in vivo in the presence of complement with a contraceptive composition comprising a human sperm inactivating amount of monoclonal antibody NUH2 and a pharmaceutically acceptable carrier, diluent or excipient. The present invention also provides the above-described contraceptive composition.

In this method, the complement can be provided by its presence in the human body.

Suitable pharmaceutically acceptable carriers, diluents or excipients can readily be determined by the skilled artisan and include creams and gels currently used for vaginal contraceptives.

In a preferred embodiment, the monoclonal antibody NUH2 is added as a supplement to currently available contraceptive creams, gels, etc. in amounts and by methods readily determined by the skilled artisan.

According to the present invention, the isolated antigen which is capable of inducing anti-human sperm antibody NUH2 and which comprises the sialyl I structure can also be used to provide a method of contraception. Such a method comprises inducing an anti-sperm immune response in human females by administering a vaccine comprising: (a) a pharmaceutically effective amount of the antigen and (b) a pharmaceutically acceptable carrier, diluent or excipient. The present invention also provides the above-described contraceptive vaccine.

Doses and suitable pharmaceutically acceptable carriers, diluents and excipients can readily be determined by the skilled artisan.

The antigens of the present invention are also useful for detection of antibodies present in sera of infertile women, and this invention includes any device for such a detection system based on these structures. The phrase "based on these structures" above includes all such antigens, either natural or synthetic, carried by liposome or in solid phase, either attached to natural or synthetic polymers or glass, and includes all types of possible methods, such as ELISA, radioimmunoassay, or competitive inhibition assay using partial or whole oligosaccharide structures.

Thus, the present invention provides a method of detecting anti-sperm antibodies present in the sera of infertile human females comprising:
(a) taking a blood sample from the infertile female;
(b) contacting the blood sample with an antigen capable of specifically binding to anti-human sperm antibody NUH2 and comprising the sialyl I structure, and
(c) detecting the presence of any antigen-anti-sperm antibody complexes.

Numerous techniques for performing the above method are well known in the art as described above.

Another important application of the antigen structures is for elimination of antibody in infertile women.

In fact, examination of human sperm glycolipids revealed the presence of a series of lactosaminolipids, including those representing i, sialyl i and sialyl I structures. Nevertheless, the quantity of glycolipids representing these structures in human sperm cells seems to be relatively low, and the isolated glycolipids may not form high-affinity binding sites. The major high-affinity receptor causing inactivation of sperm motility must be a glycoprotein characterized as having lactosaminoglycan, as was previously found in fetal erythrocyte band III glycoprotein (Fukuda, M., et al (1979) *J. Biol. Chem.* 254:3700), placental fibronectin (Zhu, B., et al (1984) *J. Biol. Chem.* 259:3962), and "embryoglycan" of teratocarcinoma cells (Muramatsu, T., et al (1982). High molecular weight carbohydrates on embryonal carcinoma cells. In: Teratocarcinoma and embryonic cell interactions. T. Muramatsu, G. Gachelin, A. A. Moscona, and Y. Ikawa, editors. Academic Press, New York. 143–156). The epitope structure in such a high affinity receptor causing inactivation of sperm motility includes not only disialyl I but also sialyl i and i structures within the same macromolecule. This is obvious because the glycoprotein antigens isolated from sperm and placenta were also reactive with anti-i antibody, Dench or NCC-1004 antibody; a particularly strong activity was observed after treatment of the antigens with sialidase.

NUH2 defines binary $\alpha2\rightarrow3$ sialyl type 2 chain, i.e., sialyl-I. Thus, the presence of antibodies in the sera of infertile women directed to sperm lactosaminoglycan or lactosaminolipid could be the basis for infertility in these cases. If infertility is due to the presence of the antibody, any device for elimination of the antibody, such as passage of the blood stream through a solid phase epitope during plasmaphoresis, is a logical way to treat this disorder.

Thus, the present invention includes a method of treating infertile human females whose infertility is caused by the presence of anti-sperm antibodies in the female's sera comprising:
(a) contacting the sera ex vivo with an antigen having epitopes to anti-human sperm antibodies and comprising the sialyl I, i and sialyl i structures to thereby form an anti-sperm antibody-antigen complex between said antibodies and said antigens such that said antibodies are removed from the sera, and
(b) recycling said contacted sera to said female.

As discussed above, techniques and equipment for practicing this method are well known in the art including a method where the antigen is affixed to a solid support as well as a method wherein the antigen is not affixed to a solid support and the complex is removed from the sera by filtering prior to recycling the contacted sera to the female.

EXAMPLES

The present invention will now be described by reference to specific examples, which are not meant to be limiting.

Unless otherwise specified, all percents, ratios, etc. are by weight.

Example 1

Complement-dependent Immobilization of Sperm with Monoclonal Antibody NUH2

A complement-dependent sperm immobilization test was performed as originally described by Isojima et al (Isojima, S., et al (1972) *Am. J. Obstet. Gynecol.* 112:199) with minimal modification. Briefly, 50 $\mu$l of hybridoma supernatant or anti-i serum adequately diluted with phosphate buffered saline (PBS) containing 1% heat-inactivated fetal calf serum (FCS) was placed in each well of a 96-well Falcon 3040 microtissue culture plate, to which 50 $\mu$l of $10^6$/ml live sperm suspended in PBS containing 1% FCS was added, and, subsequently, 10 $\mu$l of guinea pig serum was added as the source of complement. After 1 hour incubation at room temperature, live sperm showing active motility were counted. In order to evaluate the sperm immobilization value of the antibody, motility rates of the sperm in the experimental wells were compared with those of sperm in control wells to which 10 $\mu$l of heat-inactivated guinea pig serum had been added. The sperm immobilization value of the antibody was calculated as C/T, where C and T were the motility rates of sperm in the control and experimental wells, respectively. A C/T value $>50$ was considered positive.

The complement used was from guinea pig serum purchased from ICN (vendor code no. 642831). This complement did not show a cytotoxic effect on fresh human sperm; however, it did show a cytotoxic effect on sialidase-treated sperm. Therefore, the test was performed with complement adsorbed on sialidase-treated sperm. The pooled sperm were mixed with 0.5 unit/ml sialidase (*Clostridium perfringens* sialidase, Sigma type X; see below), centrifuged, and washed three times with PBS. One part by volume of sialidase-treated sperm was mixed with 1 part by volume of fresh guinea pig serum containing complement, and followed by centrifugation. The supernatant was treated twice with 1 part by volume sperm. Such complement showed full activity, but had no cytotoxic effect on sialidase-treated sperm.

Sperm preparation

For the sperm preparation, a sufficient quantity of freshly ejaculated semen was diluted with PBS, and sperm cells were collected by centrifugation (3000 rpm), washed with PBS containing 1% FCS, and suspended in PBS ($10^6$/ml).

Monoclonal antibodies

In addition to IgM antibody NUH2 defining binary NeuAcα2→3Galβ1→4GlcNAc (IV$^6$NeuAcα2→3Galβ1→4GlcNAcVI$^3$NeuAcnLc$_6$; sialyl-I) other monoclonal antibodies used were: (i) IgM antibody 1B9 defining NeuAcα2→6Galβ1→4GlcNAc (Hakomori, S. et al (1983) *J. Biol. Chem.* 258:11819); (ii) IgM antibody 1B2 defining Galβ1→4GlcNAc (Young, W. W. Jr. et al (1981) *J. Biol. Chem.* 256:10967); and (iii) IgM antibody C6 defining binary Galβ→4GlcNAc (IV$^6$Galβ1→4GlcNAcnLc$_6$; I) (Fenderson, B. A. et al (1986) *Molec. Immun.* 23:747). Two anti-i antisera, Bostrum and Dench, were provided by Mrs. Osaki of Puget Sound Blood Bank, Seattle, Wash. *Glycosidase treatment of sperm cells*

Sperm cells fixed on plastic plates, as previously described, were treated with *Clostridium perfringens* sialidase, jackbean β-galactosidase (Li, Y.-T., and S.-C. Li. (1972). *Meth. Enzymol.* 28:702) (Sigma type X, Sigma Chemical Co., St. Louis Mo.), or with both enzymes. Aliquots of 25 μl of sialidase (0.1 unit/ml) in 20 mM acetate buffer, pH 5.5, were added to each well and incubated for 16 hours at 37° C. In order to observe the effect of sialidase on the sperm immobilization test, a suspension of $4 \times 10^7$ sperm in 0.5 ml of PBS containing 1% heat-inactivated FCS was mixed with 1 unit/ml of *C. perfringens* sialidase and incubated for 1 hour at 37° C. Sperm motility was unchanged after this treatment, compared to the same treatment without sialidase. Endo-β galactosidase of *Escherichia freundii*, which preferentially cleaves unbranched type 2 chains or their sialylated derivatives (Fukuda, M. N. et al (1978) *J. Biol. Chem.* 253:6814), was donated by Dr. Minoru Fukuda (La Jolla Cancer Research Foundation, Calif.). The enzyme solution containing 0.1 unit/ml in 100 mM acetate buffer, pH 5.0, was prepared and 50 μl was added to sperm fixed on plastic wells after sialidase treatment as described above.

The results are shown in Table I below:

TABLE I

Complement-dependent sperm immobilizing test of various monoclonal antibodies

| Antibody | non-treated sperm | sialidase-treated sperm |
|---|---|---|
| NUH2 (sup)* | X1024 | — |
| C6 (sup)* | — | x512 |
| 1B2 (sup)* | — | x2048 |
| 1B9 (sup)* | — | — |
| Dench (serum)** | — | x4056 |
| Bostrum (serum)** | — | x4056 |

*sup, culture supernatant of hybridoma containing 18 μg IgM/ml for NUH2; 25 μg IgM/ml for C6; 8 μg IgM/ml for 1B2; and 1.9 μg IgM/ml for 1B9.
**serum of myeloma patients, Dench and Bostrum, containing anti-i myeloma protein.
— no activity even at 100 times dilution.

From Table I it can be seen that only the antibody NUH2, which defines the disialyl I structure, inhibited the motility of intact sperm in the presence of complement. However, when sialidase-treated sperm (which still showed active motility) where used, antibodies C6, 1B2, Dench and Bostrum also showed inhibition of the motility. It is clear that the receptors in intact sperm that are susceptible to complement-dependent immobilization consist of at least sialyl-I (as defined by NUH2), whereas those in sialidase-treated sperm may consist of any type 2 chain terminal structure, as defined by Bostrum, Dench, 1B2, or C6.

Further, the sperm cell reactivity with NUH2 was abolished after sialidase treatment. In contrast, the reactivity with anti-i (Dench and Bostrum), anti-N-acetyllactosamine (1B2), and anti-I (C6) was enhanced after sialidase treatment, as shown in FIGS. 1A–1E (Data for Bostrum not shown).

Example 2

Epitope Specificity of Monoclonal Antibody NUH2

The reactivity of NUH2 was determined by solid-phase antibody-binding assays on glycolipid coated plastic wells by known methods (Kannagi, R., et al (1983) *Cancer Res.* 43:4997).

The glycolipids used were GM$_2$ ganglioside (II$^3$NeuAc Gg$^3$); sialyl 2→3 paragloboside (IV$^3$-NeuAcnLc$_4$) (Siddiqui, B., and S. Hakomori (1973) *Biochim. Biophys. Acta.* 330:147); sialyl 2→6 paragloboside (IV$^6$NeuAcnLc$_4$); sialyl 2→3 norhexaosylceramide (VI$^3$ NeuAcnLc$_6$); sialyl 2→6 norhexaosylceramide (VI$^6$ NeuAcnLc$_6$); sialidase-treated disialosyl I, i.e., I (IV$^6$Galβ1→4GlcNAcnLc$_6$); sialidase-treated fraction 90–102 ganglioside (VI$^6$Galβ1→4GlcNAcIV$^6$-Galβ1→4GlcNAcnLc$_8$); sialidase-treated fraction 72–77 ganglioside (IV$^6$Galβ1→4GlcNAcnLc$_8$); 2→3 disialyl lactoisooctaosylceramide (VI$^3$NeuAcIV$^6$-NeuAc2→3Galβ1→4GlcNAcnLc$_6$; disialyl I) (Okada, Y., R. et al (1984) *J. Immunol.* 133:835; Kundu, S. K., et al (1983) *J. Biol. Chem.* 258:13857; fraction 90–102 ganglioside (isolated from placenta) which contains the disialyl I structure (VIII$^3$NeuAcVI$^6$NeuAc2→3Galβ1→4GlcNAcIV$^6$NeuAc2→3Galβ1→4GlcNAcnLc$_8$) and fraction 72–77 ganglioside (isolated from placenta) which does not contain the disialyl I structure (VIII$^3$NeuAcIV$^6$NeuAc2→3Galβ1→4GlcNAcnLc$_8$).

Sialyl 2-3 and 2-6 norhexasoylcaramide has been described by Watanabe K. et al (1979) *J. Biol. Chem.* 254:8223–8229, and these structures particularly lactonorhexaosylceramide as i are described by Nieman, H. et al (1978) *Biochem. Biophys. Res. Comm.* 81:1286–1293. Sialyl I and I glycolipids have been described by Watanabe K. and Hakomori S. (1979) *J. Biol. Chem.* 254:3221-3228 and by Okada Y. et al (1984) *J. Immunol.* 133:835-842 The structures of fraction 90-102 ganglioside and of fractions 72-77 ganglioside are new structures and have not been published previously. All other gangliosides and glycolipids have been described by Hakomori, S. "Sphingolipid Biochemistry" p 1-165 1983 Plenum Press, New York and London.

The method of preparation has been described previously (Hakomori, S. (1983) Chemistry of glycosphingolipids. In: Handbook of lipid research, Vol. 3: Sphingolipid biochemistry. J. N. Kanfer, and S. Hakomori, editors. Plenum, New York. 1-165). Briefly, tissues were extracted by isopropanol-hexane-water 55:30:25 (v/v/v), followed by Folch's partition repeated three times, DEAE cellulose chromatography, high performance liquid chromatography (HPLC) on porous silica gel column (Iatrobeads 6RS8010), and finally purification on high performance thin layer chromatography (HPTLC) as free state or as acetate. Each glycolipid preparation was homogeneous on HPTLC, and some of their structures were identified by nuclear magnetic resonance (NMR) and fast-atom bombardment mass spectrometry (FAB-MS).

Fraction 90-102 ganglioside was characterized as having a long-chain ganglioside with the same epitope as disialyl I; fraction 72-77 ganglioside did not contain the disialyl I structure.

Figure 1A:
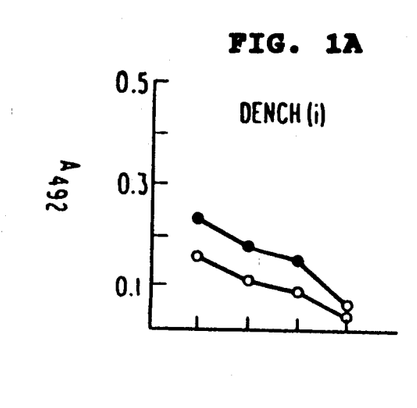
In FIG. 1A "Dench" defines structure i (unbranched poylactosamine)
Figure 1B:
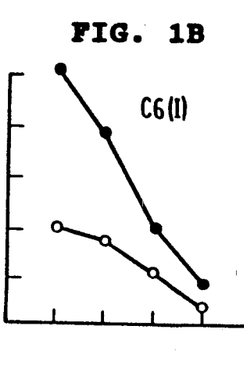
Figure 1C:
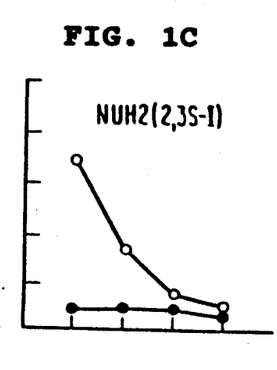
In FIG. 1C NUH2 reacts with 2→3 disialyl-I.
Figure 1D:
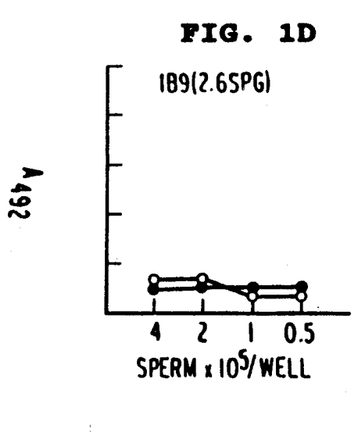
Figure 1E:
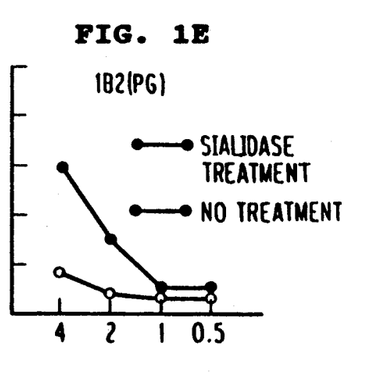
Figure 2:
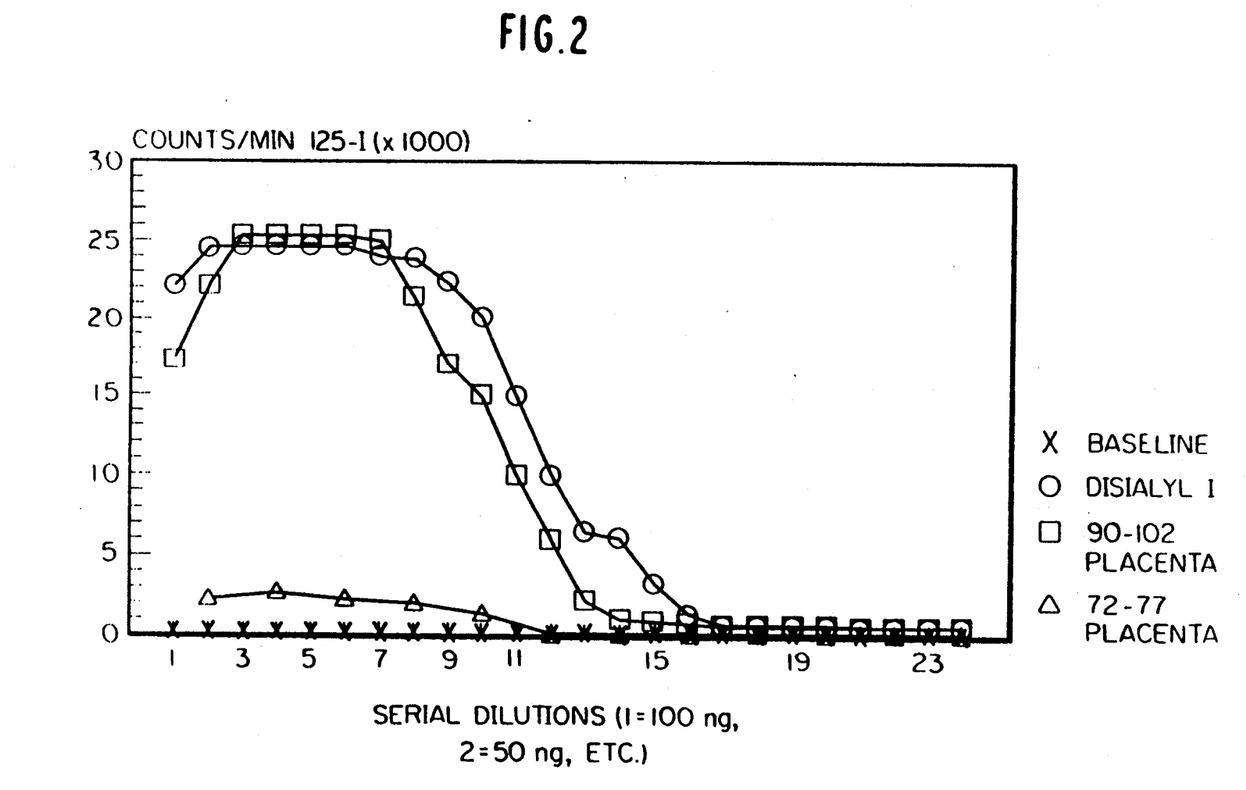

The results are shown in FIG. 2.

In FIG. 2, the ordinate represents $^{125}$I-labeled antibody binding and the abscissa represents serial dilutions of antigen, wherein 1 is 100 ng antigen per well, 2 is 50 ng antigen per well, etc.

The baseline represents no reactivity and includes reactions with $GM_2$ ganglioside, sialyl 2→3 paragloboside, sialyl 2→6 paragloboside, sialyl 2→3 norhexaosylceramide, sialyl 2→6 norhexaosylceramide, sialidase-treated disialosyl I, sialidase-treated fraction 90-102 ganglioside and sialidase-treated fraction 72-77 ganglioside.

High reactivities were observed with disialyl I and fraction 90-102 ganglioside (from placenta). Fraction 72-77 ganglioside (from placenta) showed only very weak activity.

The results indicate that monoclonal antibody NUH2 is specific for the disialyl I epitope. The results also indicate that the disialyl structure linked to a binary branched type 2 chain is essential for reactivity of monoclonal antibody NUH2.

Example 3

Isolation and Partial Characterization of Sperm Antigen Defined by Monoclonal Antibody NUH2

Seven hundred ml of semen was centrifuged at room temperature for 20 min at 3000 rpm. The sperm cell pellet was washed with PBS. The supernatant, which contained seminal fluid, and the sediment, which contained sperm cells, were used separately for antigen extraction. The sperm pellet (approximately 6.2 g) was extracted with 150 ml of isopropanol-hexane-water (55:20:25, v/v/v) three times by homogenization. In each extraction, the residue was centrifuged, and the extract was evaporated to dryness in a rotary evaporator. The dried residue was treated with chloroform-methanol (2:1, v/v), and the chloroform-methanol extract was partitioned with water according to established procedure (Hakomori S (1983), In *Handbook of Lipid Research, Vol. 3, Sphingolipid Biochemistry* (Kanfer JN & Hakomori S, eds.), Plenum, N.Y., pp. 1-165). The total polar glycolipid fraction present in the upper phase of the Folch partition was further purified by reverse phase chromatography on a C-18 silica gel column, DEAE-Sephadex A25 column, and high performance liquid chromatography on Iatrobeads 6RS-8010. Each glycolipid was further purified by high performance thin-layer chromatography. All these procedures have been described in the above references as well as in more recent publications (Hakomori, et al. (1984) *J. Biol. Chem.* 259:4672-4680; Fukushi et al. (1984) *J. Biol. Chem.* 259:10511-10517; Nudelman et al. (1986) *J. Biol. Chem.* 261:5487-5495; Nudelman et al. (1986) *J. Biol. Chem.* 261:11247-11253). Separated antigens were immunostained with monoclonal antibodies, NUH2, as well as 1B2 defining sialyl 2→6i, 1B9 defining sialyl 2→6Gal, SH1 defining Le$^x$, SH2 defining dimeric Le$^x$, FH6 defining sialyl difucosyl type 2 chains, NCC-1004 defining i, C6 defining I and M2590 defining $GM_3$ ganglioside.

TLC immunostaining of glycolipids was performed on high performance thin layer chromatography (HPTLC) (Baker Chemical Co., Phillipsburg, N.J.; or Whatman Company, Kent, England), according to a modified method (Kannagi, R., et al (1983). *J. Biol. Chem.* 258:8934; Kannagi, R., et al (1982) *J. Biol. Chem.* 257:14865) of a procedure originally described by Magnani et al (Magnani, J. L. et al (1980) *Anal. Biochem.* 109:399). Briefly, the HPTLC plate, after development, was treated with 3% bovine serum albumin (BSA) in PBS, followed by reaction with the primary antibody at 4° C. overnight. Subsequently, the plate was treated with the secondary antibody at room temperature for 1 hour, and $^{125}$I-protein A for 0.5 hr, then washed 3 times with PBS, dried, and subjected to autoradiography.

The results were that a positive reaction was observed with NUH2, 1B2, NCC-1004 and C6. The bands reactive with the last three antibodies increased greatly after sialidase treatment.

The sperm cell pellet, after extraction with isopropanol-hexane-water as above, was solubilized by homogenization with 1% Triton X-100 containing 8 M urea, 0.1 M Tris-HCl buffer, pH 8.5. The pellet (6.2 g) was homogenized with 280 ml three times. The extract was precipitated with 65% ammonium sulfate and centrifuged for 15 min at 3700 rpm. The pellet was dissolved in a minimum quantity of distilled water, and absolute ethanol was added up to 80% and left overnight at 0° C. The precipitate was centrifuged at 15,000 rpm at 4° C. for 30 min, the pellet was dissolved in 0.01 M Tris-HCl, pH 8.5, and the solution was gel-filtrated over a Sephadex CL-4B column equilibrated with the same buffer solution.

Figure 3:
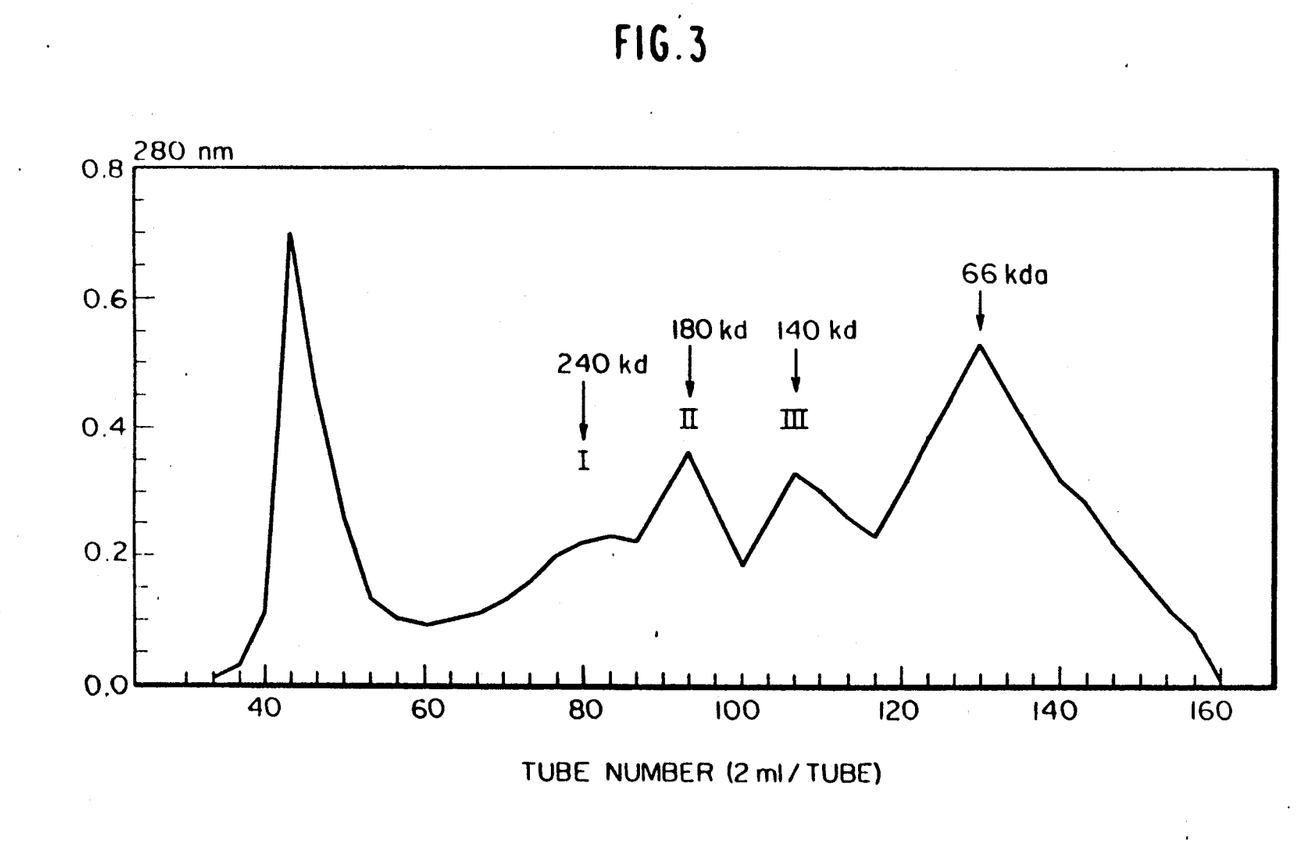
FIG. 3 is a pattern obtained from isolation of NUH2-defined antigen on a Sepharose CL-4B-200 column. Sperm extracts were placed on a Sepharose CL-4B-200 column. The elution pattern, monitored by absorption at 280 nm, is shown. Relative molecular weights of peaks I, II and III are 240, 180, and 140 KDa respectively.

The elution pattern, shown in FIG. 3, was monitored by absorption at 280 nm. Fractions present in peaks I, II and III were strongly reactive (as measured by an antibody blotting assay) with monoclonal antibody NUH2. The void peak was active, but relatively weakly.

The relative molecular weights of peaks I, II and III are 240, 180 and 140 KDa, respectively.

Figure 4:
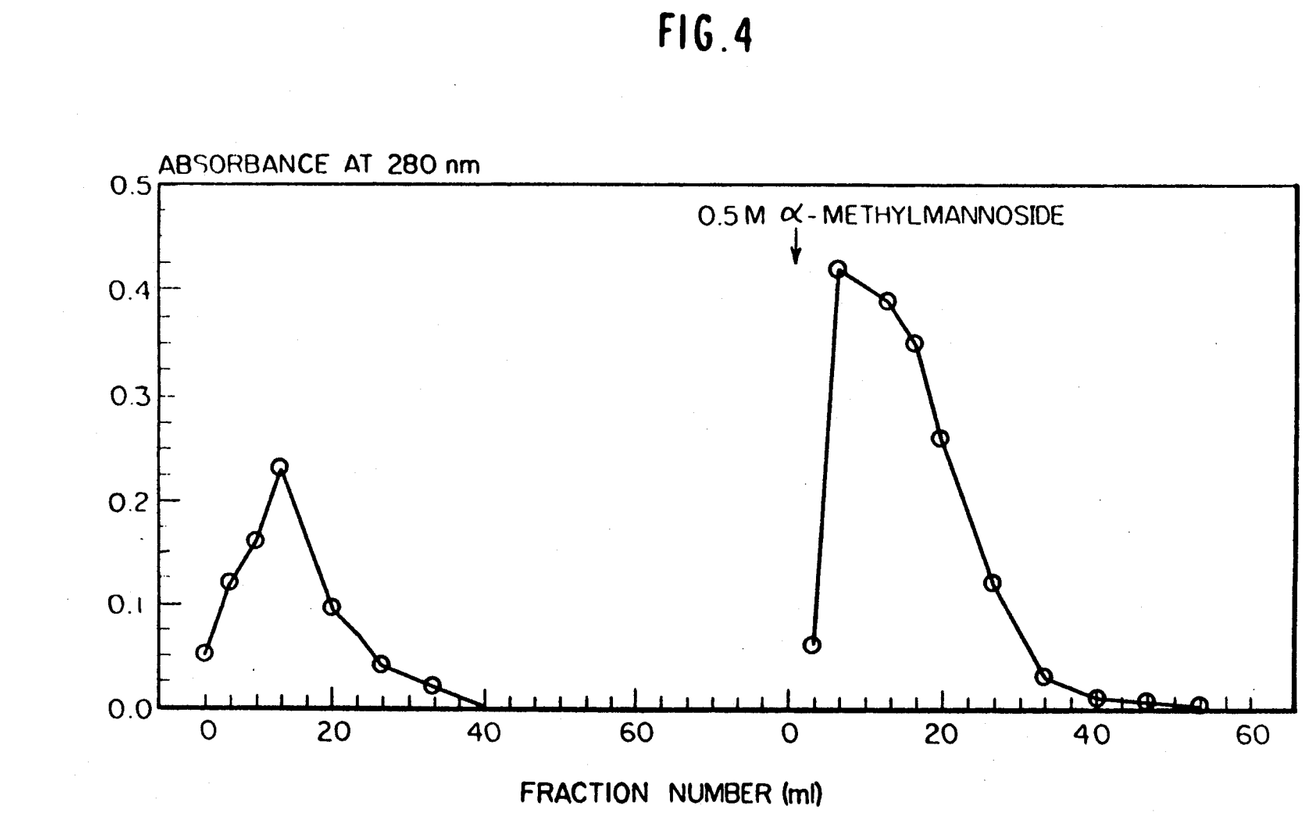
FIG. 4 is a pattern obtained from isolation of NUH2-defined antigen on a Con A Sepharose column. Pooled fractions (tube #s 60–118) from Sepharose CL-4B-200 gel filtration were placed on a Con A Sepharose column and eluted with 0.5M methyl α-D-mannopyranoside. NUH2-positive glycoprotein was concentrated in this peak.

These peaks were further purified on a Con A-Sepharose 4B column. All the NUH2-reactive antigens were adsorbed on the Con A-Sepharose column and were eluted with 0.5 M methyl-α-glucopyranoside. These antigens with different molecular weights were concentrated into one peak as shown in FIG. 4 and are characterized as having the common epitope sialyl-I defined by monoclonal antibody NUH2.

The Con A-Sepharose column purified antigens were also reacted with anti-i antibody NCC-1004 (Hiroshi, S. et al (1986) *J. Immunol.* 136:4163-4168); anti-i Dench antibody (Nieman, H. et al (1978) *Biochem. Biophys. Res. Commun.* 81: 1286-1293); and anti-I antibody C6.

The results were that a positive reaction was observed with NUH2 (anti-sialyl I), NCC-1004 (anti-i), and Dench antibody (anti-i) thereby indicating that the antigen contains the epitopes sialyl I and i. Further, the reactivity of the antigens with C6, Dench and NCC-1004 was greatly enhanced by sialidase treatment thereby indicating that the fractions contain sialyl i as well as i and sialyl I.

Chemical analysis of the antigens defined by antibody NUH2 was carried out by nuclear magnetic resonance spectroscopy and mass spectrometry of the permethylated compound.

The structure of the antigen was confirmed to be a series of compounds carrying the sialyl I structure, the i structure and the sialyl i structure.

While the invention has been described in detail and with reference to specific embodiments thereof, it will be apparent to one skilled in the art that various changes and modifications can be made therein without departing from the spirit and scope thereof.

What is claimed is:

1. Monoclonal antibody NUH2 secreted by a hybridoma having ATCC deposit no. HB 9762.

2. A method of inactivating human sperm motility comprising contacting said sperm with monoclonal antibody NUH2 in the presence of complement.

3. A method of vaginal contraception comprising contacting human sperm in the presence of complement with a contraceptive composition comprising a human sperm inactivating amount of monoclonal antibody NUH2, and a pharmaceutically acceptable carrier, diluent or excipient.

4. The method of claim 3, wherein said vaginal contraceptive composition is a vaginal cream or gel.

5. A vaginal contraceptive composition comprising a human sperm inactivating amount of monoclonal antibody NUH2, secreted by a hybridoma having ATCC deposit no. HB 9762 and a pharmaceutically acceptable carrier, diluent or excipient.

6. The vaginal contraceptive composition of claim 5, wherein the pharmaceutically acceptable carrier is a vaginal cream or gel.

7. A hybridoma capable of producing monoclonal antibody NUH2 and having ATCC deposit no. HB 9762.

* * * * *